(12) United States Patent
Manero et al.

(10) Patent No.: US 7,009,047 B2
(45) Date of Patent: Mar. 7, 2006

(54) ETHANE-1,2-DIAMINIUM BIS[(2R)-2-BROMO-3-PHENYLPROPANOATE], PROCESSES FOR ITS PREPARATION AND ITS USE

(75) Inventors: Javier Manero, Liederbach (DE); Tobias Metzenthin, Hofheim (DE); Rainer Gauler, Liederbach (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 258 days.

(21) Appl. No.: 10/389,872

(22) Filed: Mar. 17, 2003

(65) Prior Publication Data

US 2004/0010039 A1    Jan. 15, 2004

Related U.S. Application Data

(60) Provisional application No. 60/397,456, filed on Jul. 19, 2002.

(30) Foreign Application Priority Data

Mar. 19, 2002 (DE) ................. 102 12 198

(51) Int. Cl.
*C07D 471/04* (2006.01)
*C07D 497/04* (2006.01)
*C07C 53/134* (2006.01)
*C07C 327/32* (2006.01)

(52) U.S. Cl. .............. 540/488; 540/521; 540/522; 562/496

(58) Field of Classification Search ................ 540/488, 540/521, 522; 562/496
See application file for complete search history.

(56) References Cited

FOREIGN PATENT DOCUMENTS

| EP | 0 481 522 A1 | 4/1992 |
| EP | 1 056 715 B1 | 6/2002 |
| WO | WO 99/42438 | 8/1999 |

OTHER PUBLICATIONS

Robl Jeffrey A et al., Vasopeptidase Inhibitors: Incorporation Of Geminal And Spirocyclic Substituted Azepinones In Mercaptoacyl Depeptides, Journal Of Medicinal Chemistry, (1999), vol. 42, pp. 305-311.

Robl Jeffrey A et al., Dual Metalloprotease Inhibitors: Mercaptoacetyl-Based Fused Heterocyclic Dipeptide Mimetics As Inhibitors Of Angiotensin-Converting Enzyme And Neutral Endopeptidase, Journal Of Medicinal Chemistry, (1997), vol. 40, pp. 1570-1577.

*Primary Examiner*—Bruck Kifle
(74) *Attorney, Agent, or Firm*—Karen I. Krupen

(57) ABSTRACT

The present invention relates to ethane-1,2-diaminium bis [(2R)-2-bromo-3-phenyl-propanoate], the preparation of ethane-1,2-diaminium bis[(2R)-2-bromo-3-phenyl-propanoate] from (2R)-2-bromo-3-phenylpropionic acid and ethylenediamine in 2-propanol, and the use of ethane-1,2-diaminium bis[(2R)-2-bromo-3-phenyl-propanoate] for the preparation of ACE/NEP inhibitors.

17 Claims, No Drawings

ETHANE-1,2-DIAMINIUM BIS[(2R)-2-BROMO-3-PHENYLPROPANOATE], PROCESSES FOR ITS PREPARATION AND ITS USE

BACKGROUND OF THE INVENTION

Chiral compounds are employed as structural units for the synthesis of pharmaceutical active compounds. It is desirable that these compounds are stable on storage and moreover can be prepared and purified simply in order to ensure constant quality, to avoid frequent checks of the materials for keeping a record of the product quality, to avoid the necessity for cold-storage depots and/or refrigerated transport, to guarantee easy filling in production plants and/or to guarantee the simple cleaning of used containers.

Viscous oils can often only be poured into another container or weighed exactly with difficulty. Moreover, the purification of oils or viscous liquids can in many cases only be carried out with considerable outlay in terms of apparatus. In addition, oils can exhibit nonoptimal behaviour on dissolving in solvents, for which reason the mixing of liquids having different densities and viscosities must be monitored with particular care.

(2R)-2-Bromo-3-phenylpropionic acid is a viscous oil which has several of the disadvantageous properties listed above. Use of (2R)-2-bromo-3-phenylpropionic acid on the industrial scale is therefore associated with difficulties and additional costs.

SUMMARY OF THE INVENTION

It is the object of the present invention to prepare (2R)-2-bromo-3-phenylpropionic acid in a form which does not have the abovementioned disadvantages and which can be employed in industrial syntheses.

The object is achieved according to the invention by the preparation of the salt (ethane-1,2-diaminium bis[(2R)-2-bromo-3-phenylpropanoate]) in pure form and with retention of the enantiomeric purity.

Surprisingly, it has been found that a salt (ethane-1,2-diaminium bis[(2R)-2-bromo-3-phenylpropanoate]) can be isolated in good yield and excellent chemical and enantiomeric purity from (2R)-2-bromo-3-phenylpropionic acid and ethylenediamine in 2-propanol in the stoichiometry 2:1.

The present application accordingly relates to ethane-1,2-diaminium bis[(2R)-2-bromo-3-phenylpropanoate].

The invention further relates to a process for the preparation of ethane-1,2-di-aminium bis[(2R)-2-bromo-3-phenylpropanoate], which comprises a) mixing (2R)-2-bromo-3-phenylpropionic acid, ethylenediamine and 2-propanol, which results in ethane-1,2-diaminium bis[(2R)-2-bromo-3-phenylpropanoate] crystallizing out of solution, and b) isolating the crystallized ethane-1,2-diaminium bis[(2R)-2-bromo-3-phenyl-propanoate].

Preferably, the ethane-1,2-diaminium bis[(2R)-2-bromo-3-phenylpropanoate] prepared in the process according to the invention has a higher purity than the starting material (2R)-2-bromo-3-phenylpropionic acid.

Preferably, the process according to the invention proceeds with retention of or an increase in the enantiomeric purity.

In step b), the crystallized ethane-1,2-diaminium bis[(2R)-2-bromo-3-phenyl-propanoate] can be isolated by filtering it off or filtering it off with suction; optionally the product filtered off with suction or filtered off can then be washed using 2-propanol and dried.

The starting material (2R)-2-bromo-3-phenylpropionic acid is obtainable, for example, from the company Zambon Group spa (I-20091 Bresso, Italy) or the company Kaneka (Osaka, Japan).

Ethane-1,2-diaminium bis[(2R)-2-bromo-3-phenylpropanoate] can be used, for example, for a process for the production of ACE/NEP inhibitors, for example reacted to give a compound of the formula (I),

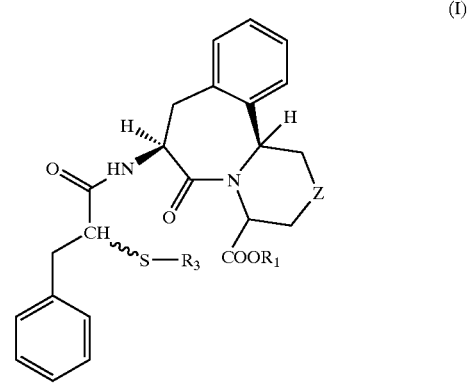

(I)

wherein $R_1$ is H, $C_1$–$C_4$-alkyl, or an aryl-Y— group, where Y is a single bond or $C_1$–$C_4$-alkyl, $R_3$ is H, acetyl or benzoyl, and Z is $(CH_2)_n$, —O—, S, $NR_6$ or N—C(O)$R_7$, where n is an integer 0 or 1, $R_6$ is H, $C_1$–$C_4$-alkyl or an aryl-Y— group, and $R_7$ is $CF_3$, $C_1$–$C_{10}$-alkyl or an aryl-Y— group, wherein, preferably, $R_1$ is H, $R_3$ is H or acetyl, and Z is $(CH_2)_n$, and n is 0, and wherein the CH—$SR_3$ group can have the (R) or the (S) configuration, and preferably has the (S) configuration, and wherein the compound of the formula (I) is preferably described by a compound of the formula (Ia)

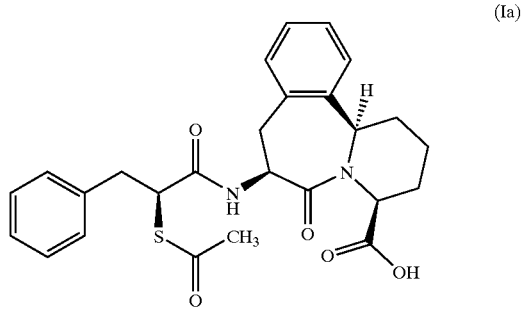

(Ia)

or of the formula (Ib)

-continued

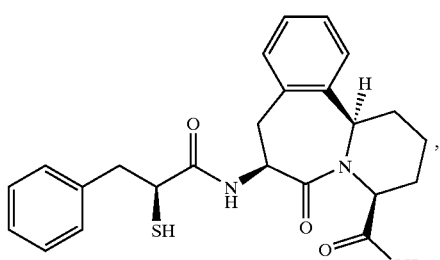
(Ib)

characterized in that firstly (2R)-2-bromo-3-phenylpropionic acid is synthesized from ethane-1,2-di-aminium bis[(2R)-2-bromo-3-phenylpropanoate] with addition of an acid, either intermediately or in a separate step according to methods known per se, and subsequently either (2R)-2-bromo-3-phenylpropionic acid is reacted with a compound of the formula (II)

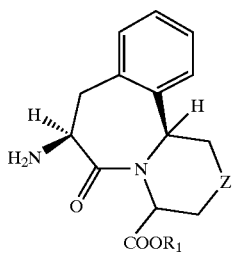
(II)

and a thio reactant to give a compound of the formula (I), and when $R_3$ of formula (I) is acetyl, or benzoyl, then optionally converting a compound of formula (I) to a compound of formula (I) wherein $R_3$ is H, where converting a compound of formula (I), wherein $R_3$ is acetyl or benzoyl, to a compound of formula (I) wherein $R_3$ is H, can be carried out using known techniques for converting a thioester group to a thiol group, particularly known techniques for removing an acetyl or benzoyl protecting group to afford a free thiol compound (see T. W. Green and P. G. M. Wuts in "Protective Groups in Organic Chemistry" John Wiley and Sons, 1991, incorporated herein by reference in its entirety), or (2R)-2-bromo-3-phenylpropionic acid is reacted as, for example, in European patent application EP 1056715 to give (S)-2-(acetylthio)-3-phenylpropionic acid and subsequently reacted as described, for example, in European Patent EP 481522 with a compound of the formula (II) to give a compound of the formula (I), and the thioacetate is optionally reacted to give the free thiol. European patent application EP 1056715 and European Patent EP 481522 are incorporated herein by reference, in their entirety.

"Thio reactant" as used herein means a thio reactant that, when reacted with a 2-bromo-3-phenylpropionamide compound obtained from (2R)-2-bromo-3-phenylpropionic acid and a compound of formula II, affords a compound of formula I, or when reacted with (2R)-2-bromo-3-phenylpropionic acid, affords (S)-2-(acetylthio)-3-phenylpropionic acid, for example. Particular examples of thio reactants include, thioacetate and thiobenzoate. It is well within the knowledge of the skilled artisan which thio reactant to choose to convert a 2-bromo-3-phenylpropionamide compound obtained from (2R)-2-bromo-3-phenylpropionic acid and a compound of formula II into a compound of formula I, or to convert (2R)-2-bromo-3-phenylpropionic acid into (S)-2-(acetylthio)-3-phenylpropionic acid. For example, using similar reactants and reaction conditions to those disclosed in EP1056715, a 2-bromo-3-phenylpropionamide compound obtained from (2R)-2-bromo-3-phenylpropionic acid and a compound of formula II could be converted to its corresponding 2-(acetylthio)-3-phenylpropionamide derivative of formula I by reaction with thioacetate.

"$C_1$–$C_4$-Alkyl" denotes a saturated straight-chain or branched hydrocarbon chain of 1–4 carbon atoms and comprises, for example, methyl, ethyl, propyl, isopropyl, n-butyl, isobutyl, tert-butyl. The expression "$C_1$–$C_{10}$-alkyl" denotes a saturated straight-chain or branched hydrocarbon radical having 1–10 carbon atoms, for example methyl, ethyl, propyl, isopropyl, n-butyl, isobutyl, tert-butyl, pentyl, isopentyl, hexyl, 2,3-dimethyl-2-butyl, heptyl, 2,2-dimethyl-3-pentyl, 2-methyl-2-hexyl, octyl, and 4-methyl-3-heptyl.

"Aryl-Y—" denotes an aryl radical which is substituted by a group Y, where Y can be a direct bond or a $C_1$–$C_4$-alkyl group. Aryl denotes a phenyl or naphthyl group which is unsubstituted or substituted by 1–3 substuents from the group consisting of methylenedioxy, hydroxyl, $C_1$–$C_4$-alkoxy, fluorine and chlorine. For example, the expression "aryl-Y—" denotes phenyl, naphthyl, phenylmethyl, benzyl, phenylethyl, p-methoxybenzyl, p-fluorobenzyl or p-chlorobenzyl. "Aryl-Y—" can also denote a diphenylmethyl group.

Ethane-1,2-diaminium bis[(2R)-2-bromo-3-phenylpropanoate] can furthermore be used for the preparation of the compound omapatrilate ([4S-[4α(R*), 7α, 10aβ]]-octa-hydro-4-[(2-mercapto-1-oxo-3-phenylpropyl)amino]-5-oxo-7H-pyrido[2,1-b][1,3]-thiazepine-7-carboxylic acid) of the formula (III)

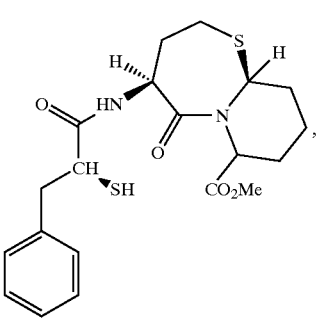
(III)

wherein firstly (2R)-2-bromo-3-phenylpropionic acid is synthesized from ethane-1,2-di-aminium bis[(2R)-2-bromo-3-phenylpropanoate] with addition of an acid, either intermediately or in a separate step according to methods known per se, and subsequently (2R)-2-bromo-3-phenylpropionic acid is reacted to give (S)-2-(acetylthio)-3-phenyl-propionic acid and, according to J. Med. Chem., 1999 (42), 305–311, or J. Med. Chem., 1997 (40) 1570–1577, in a further step (acetylthio)-3-phenylpropionic acid is reacted with a compound of the formula (IV)

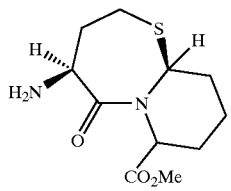

to form a compound of formula (V)

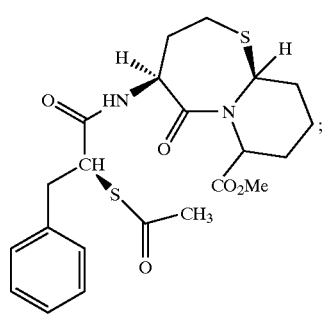

and converting a compound of formula (V) to a compound of formula (III) by normal techniques known for removing an acetyl protecting group to afford a free thiol compound. For suitable reaction conditions for removing an acetyl protecting group to afford a free thiol compound see T. W. Green and P. G. M. Wuts in "Protective Groups in Organic Chemistry" John Wiley and Sons, 1991, incorporated herein by reference in its entirety.

The acid is an organic or inorganic acid, preferably an inorganic acid, for example a mineral acid such as $H_2SO_4$ or HCl.

It has been found that when using 2-propanol as a solvent and ethylenediamine as amine the chemical purity of the product compared with the starting material increases from 92.5% to 98%; a good yield of 58% and a very good enantiomeric purity of 98.6% ee (starting from an enantiomeric purity of the starting material of 83.4% ee) can be achieved.

The present application accordingly relates to ethane-1,2-diaminium bis[(2R)-2-bromo-3-phenylpropanoate] of a chemical purity of greater than 92.5%, preferably greater than or equal to 98%.

The present application moreover relates to ethane-1,2-diaminium bis[(2R)-2-bromo-3-phenylpropanoate] of an enantiomeric purity of greater than 83.4% ee, preferably greater than or equal to 95% ee, particularly preferably greater than or equal to 98% ee.

During the addition of basic agents such as, for example, amines, an elimination of hydrogen bromide from (2R)-2-bromo-3-phenylpropionic acid can occur, cinnamic acid resulting and the enantiomeric purity of the product being lowered. Such an elimination is not observed when using ethylenediamine as an amine in 2-propanol as a solvent. The product ethane-1,2-diaminium bis[(2R)-2-bromo-3-phenylpropanoate] is therefore obtained in excellent enantiomeric purity.

Moreover, it is to be taken into consideration in the choice of solvent and amine that the product salt crystallizes from the reaction mixture in order firstly to be easily isolable and where secondly the reaction equilibrium is shifted to the side of the product.

When using other solvents and/or amines, either the purity of the product compared to the starting material is not increased, or the reaction does not proceed, or the yield is low, or an elimination takes place as a secondary reaction.

EXAMPLES

The following examples are intended to illustrate the invention in greater detail without restricting it to these embodiments.

Example 1

Synthesis of ethane-1,2-diaminium bis[(2R)-2-bromo-3-phenylpropanoate] in 2-propanol 5 g of (2R)-2-bromo-3-phenylpropionic acid (HPLC: 92.5%) were dissolved in 20 ml of 2-propanol and treated at room temperature with 0.87 g of ethylenediamine. After a stirring time of about 150 minutes, the precipitated product was filtered off with suction and washed with 2-propanol. The product was dried overnight at 45° C. in vacuo. The purity of the isolated product was 98% according to HPLC, the content of the R enantiomer 98.6%, and the yield was 58%.

Example 2

Characterization of ethane-1,2-diaminium bis[(2R)-2-bromo-3-phenylpropanoate]

The identity of ethane-1,2-diaminium bis[(2R)-2-bromo-3-phenylpropanoate] was determined by HPLC comparison with a sample of the starting material. The quality of the acid component of the salt was checked here; no cinnamic acid or other new, unknown substances were to be detected. The 1:2 stoichiometry was verified by means of a titration with 0.1N NaOH in water as a solvent: 2 pH steps were to be observed, which both exhibit the same consumption of NaOH. The specific rotation of ethane-1,2-diaminium bis[(2R)-2-bromo-3-phenylpropanoate] was $[\alpha]^{20}_D=+5.6°$ (c=2 in DMF); the melting point was 147° C.

TABLE 1

$^1$H-NMR data of the compound ethane-1,2-diaminium bis[(2R)-2-bromo-3-phenylpropanoate] (chemical shifts)

| Group within [phenyl-$CH_2$—CHBr—$COO^-$] [$^+H_3N$—$CH_2$—$CH_2$—$NH_3^+$] | $^{13}$C δ (ppm) | $^1$H δ (ppm) |
|---|---|---|
| —COO— | 176.24 | — |
| —CHBr— | 52.52 | 4.39 t |
| —$CH_2$— | 41.03 | 3.30 dd |
|  |  | 3.15 dd |
| phenyl- | 137.75 | 7.26 d |
|  | 128.73 | 7.32 t |
|  | 128.18 | 7.26 t |
|  | 126.59 |  |
| $^+H_3N$—$CH_2$—$CH_2$—$NH_3^+$ | 36.04 | 3.28 s |

Multiplicities:
s = singlet, d = doublet, t = triplet, dd = double doublet

Example 3

Attempt at Synthesis of ethane-1,2-diaminium bis[(2R)-2-bromo-3-phenylpropanoate] in ethyl acetate 5 g of (2R)-2-bromo-3-phenylpropionic acid (HPLC: 92.5%) were dissolved in 20 ml of ethyl acetate and treated at room temperature with 0.87 g of ethylenediamine. After a stirring time about 150 minutes, no precipitation of the product was observed. An HPLC analysis of the solution showed that (2R)-2-bromo-3-phenylpropionic acid was present unchanged.

Example 4

Attempt at Synthesis of cyclohexylamine [(2R)-2-bromo-3-phenylpropanoate] in 2-propanol 2.38 g of (2R)-2-bromo-3-phenylpropionic acid (HPLC: 92.5%) were dissolved in 15 ml of 2-propanol and treated at room temperature with 0.65 g of cyclohexylamine. After a stirring time of about 150 minutes, the precipitated product was filtered off with suction, washed with 2-propanol and dried overnight at 45° C. in vacuo. The purity of the isolated product was 92% according to HPLC. Among the impurities, cinnamic acid was also found. The yield was only 22%.

Example 5

Attempt at Synthesis of triethylammonium [(2R)-2-bromo-3-phenylpropanoate] in ethyl acetate 5 g of crude (2R)-2-bromo-3-phenylpropionic acid (HPLC: 92.5%) were dissolved in 20 ml of ethyl acetate and treated at room temperature with 2.7 ml of triethylamine. After a stirring time of about 150 minutes, no precipitation of the product was to be observed. An HPLC analysis of the solution showed that the (2R)-2-bromo-3-phenyl-propionic acid had reacted completely to give cinnamic acid.

Example 6

Synthesis of dicyclohexylammonium [(2R)-2-bromo-3-phenylpropanoate] in 2-propanol 5 g of (2R)-2-bromo-3-phenylpropionic acid (HPLC: 92.5%) were dissolved in 20 ml of 2-propanol and treated at room temperature with 4.25 g of dicyclohexylamine. After a stirring time of about 150 minutes, the precipitated salt was filtered off with suction and washed with 2-propanol. The product was dried overnight at 45° C. in vacuo. The purity of the isolated product was 94% according to HPLC, the yield was 44%.

Example 7

Synthesis of dicyclohexylammonium [(2R)-2-bromo-3-phenylpropanoate] in ethyl acetate 5 g of (2R)-2-bromo-3-phenylpropionic acid (HPLC: 92.5%) were treated at room temperature with 4.25 g of dicyclohexylamine in 20 ml of ethyl acetate. After a stirring time of about 150 minutes, the precipitated salt was filtered off with suction and washed with ethyl acetate. The product was dried overnight at 45° C. in vacuo. The purity of the isolated product was only 86% according to HPLC. Among the impurities, cinnamic acid was also found. The yield was 32%.

Example 8

Synthesis of dicyclohexylammonium [(2R)-2-bromo-3-phenylpropanoate] in toluene 5 g of (2R)-2-bromo-3-phenylpropionic acid (HPLC: 92.5%) were treated with 4.25 g of dicyclohexylamine in 20 ml of toluene at room temperature. After a stirring time of about 150 minutes, the precipitated salt was filtered off with suction and washed with toluene. The product was dried overnight at 45° C. in vacuo. The purity of the isolated product was only 81% according to HPLC. Among the impurities, cinnamic acid was also found. The yield was 31%.

Example 9

Attempt at Synthesis of triethylammonium [(2R)-2-bromo-3-phenylpropanoate] in toluene 5 g of (2R)-2-bromo-3-phenylpropionic acid (HPLC: 92.5%) were treated at room temperature with 2.7 ml of triethylamine in 20 ml of toluene. After a stirring time of about 150 minutes, no precipitation of the product was to be observed. An HPLC analysis of the solution showed that the (2R)-2-bromo-3-phenylpropionic acid had reacted completely to give cinnamic acid.

Example 10

Synthesis of dicyclohexylammonium [(2R)-2-bromo-3-phenylpropanoate] in diisopropyl ether 5 g of (2R)-2-bromo-3-phenylpropionic acid (HPLC: 92.5%) were treated at room temperature with 4.25 g of dicyclohexylamine in 20 ml of diisopropyl ether. After a stirring time of about 150 minutes, the precipitated salt was filtered off with suction and washed with diisopropyl ether. The product was dried overnight at 45° C. in vacuo. The purity of the isolated product was only 85% according to HPLC. Among the impurities, cinnamic acid was also found. The yield was 55%.

Example 11

Synthesis of dicyclohexylammonium [(2R)-2-bromo-3-phenylpropanoate] in ethanol 5 g of (2R)-2-bromo-3-phenylpropionic acid (HPLC: 92.5%) were treated in 20 ml of ethanol at room temperature with 4.25 g of dicyclohexylamine. After a stirring time of about 150 minutes, the precipitated salt was filtered off with suction and washed with ethanol. The product was dried overnight at 45° C. in vacuo. The purity of the isolated product was 96% according to HPLC. Among the impurities, cinnamic acid was also found. The yield was only 12%.

Example 12

Attempt at synthesis of N,N,N',N'-tetramethyl-ethane-1,2-diaminium bis[(2R)-2-bromo-3-phenylpropanoate] in 2-propanol 5 g of (2R)-2-bromo-3-phenylpropionic acid (HPLC: 92.5%) were dissolved in 20 ml of 2-propanol and treated at room temperature with 1.39 g of tetramethylethylene-diamine. After a stirring time of about 150 minutes, no precipitation of the product was to be observed. An HPLC analysis of the solution showed that (2R)-2-bromo-3-phenylpropionic acid was present unchanged.

Example 13

Attempt at synthesis of N,N,N',N'-tetramethyl-ethane-1,2-diaminium bis[(2R)-2-bromo-3-phenylpropanoate] in toluene 5 g of (2R)-2-bromo-3-phenylpropionic acid (HPLC: 92.5%) were dissolved in 20 ml of toluene and treated at room temperature with 1.39 g of tetramethylethylene-diamine. After a stirring time of about 150 minutes, no precipitation of the product was to be observed. An HPLC analysis of the solution showed that the (2R)-2-bromo-3-phenylpropionic acid had reacted completely to give cinnamic acid.

Example 14

Preparation of (R)-2-bromo-3-phenylpropionic acid from ethane-1,2-diaminium bis[(2R)-2-bromo-3-phenylpropanoate]

95.0 g of ethane-1,2-diaminium bis[(2R)-2-bromo-3-phenylpropanoate] (0.0675 mol) were introduced into a 500 ml four-necked flask having an outlet valve, and treated with 105 ml of diisopropyl ether and 105 ml of water. The resulting white suspension was adjusted from pH 6.7 to pH 1.5 using 15 ml of 30% strength hydrochloric acid, the suspension dissolving. The reaction mixture was then stirred at pH 1.5 and room temperature (about 20° C.) for 30 minutes, and the phases were separated. The organic phase was extracted once with 35 ml of water; the aqueous phase was discarded. The solvent diisopropyl ether and traces of water were removed from the organic phase by distillation. The residue was treated with 90 ml of acetone and distilled again, acetone and traces of diisopropyl ether distilling off. The yield was quantitative with respect to (R)-2-bromo-3-phenylpropionic acid.

What is claimed is:

1. A salt which is Ethane-1,2-diaminium bis[(2R)-2-bromo-3-phenylpropanoate].

2. The salt as claimed in claim 1 having a chemical purity of greater than or equal to 98%.

3. The salt as claimed in claim 1 having an enantiomeric purity of greater than 83.4% ee.

4. The salt as claimed in claim 3 having an enantiomeric purity of greater than or equal to 95% ee.

5. The salt as claimed in claim 3 having an enantiomeric purity of greater than or equal to 98% ee.

6. A process for the preparation of a crystalline salt form of the salt, ethane-1,2-diaminium bis[(2R)-2-bromo-3-phenylpropanoate], which comprises a) mixing (2R)-2-bromo-3-phenylpropionic acid, ethylenediamine and 2-propanol, whereupon the salt, ethane-1,2-diaminium bis[(2R)-2-bromo-3-phenylpropanoate], crystallizes out from the solution, and b) isolating the crystallized salt, ethane-1,2-diaminium bis[(2R)-2-bromo-3-phenylpropanoate].

7. The process as claimed in claim 6, wherein the crystalline form of the salt, ethane-1,2-diaminium bis[(2R)-2-bromo-3-phenylpropanoate], has a higher chemical purity than the starting material (2R)-2-bromo-3-phenylpropionic acid.

8. The process as claimed in claim 7, the chemical purity of the crystalline form of the salt, ethane-1,2-diaminium bis[(2R)-2-bromo-3-phenylpropanoate], is greater than 92.5 %.

9. The process as claimed in claim 7, wherein the chemical purity of the crystalline form of the salt, ethane-1,2-diaminium bis[(2R)-2-bromo-3-phenylpropanoate] is at least 98 %.

10. The process as claimed in claim 6, wherein the crystalline form of the salt, ethane-1,2-di-aminium bis[(2R)-2-bromo-3-phenylpropanoate], is isolated in process step b) by filtering off, or filtering off with suction, the crystalline salt, washing the crystalline salt with 2-propanol and drying the crystalline salt.

11. A process for the preparation of a compound of the formula (I)

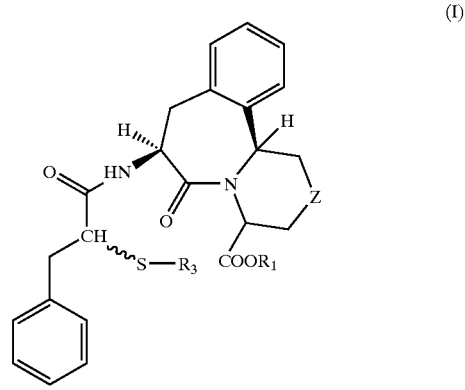

(I)

wherein $R_1$ is H, $C_1$–$C_4$-alkyl or an aryl-Y— group, where Y is a single bond or $C_1$–$C_4$-alkyl, $R_3$ is H, acetyl, or benzoyl, and Z is $(CH_2)_n$, —O—, S, $NR_6$ or N—C(O)$R_7$, where n is an integer 0 or 1, $R_6$ is H, $C_1$–$C_4$-alkyl or an aryl-Y— group, and $R_7$ is $CF_3$, $C_1$–$C_{10}$-alkyl or an aryl-Y— group, which comprises a) synthesizing (2R)-2-bromo-3-phenylpropionic acid from ethane-1,2-di-aminium bis[(2R)-2-bromo-3-phenylpropanoate] by addition of an acid; then either b) reacting (2R)-2-bromo-3-phenylpropionic acid with a compound of the formula (II)

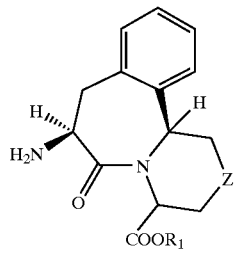
(II)

to form a 2-bromo-3-phenylpropionamide compound; then c) reacting the 2-bromo-3-phenylpropionamide compound with a thio reactant to give a compound of the formula (I); and d) when $R_3$ of formula (I) is acetyl or benzoyl, then optionally converting a compound of formula (I) to a compound of formula (I), wherein $R_3$ is H; or e) reacting (2R)-2-bromo-3-phenylpropionic acid with a thio reactant to give (S)-2-($R_3$-thio)-3-phenylpropionic acid, wherein $R_3$ is acetyl or benzoyl; then f) reacting (S)-2-($R_3$-thio)-3-phenylpropionic acid with a compound of the formula (II) to give a compound of the formula (I); and g) when $R_3$ of formula (I) is acetyl or benzoyl, then optionally converting a compound of formula (I) to a compound of formula (I) wherein $R_3$ is H.

12. The process as claimed in claim 11 wherein the compound of the formula (I) is described by a compound of the formula (Ia)

(Ia)

or of the formula (Ib)

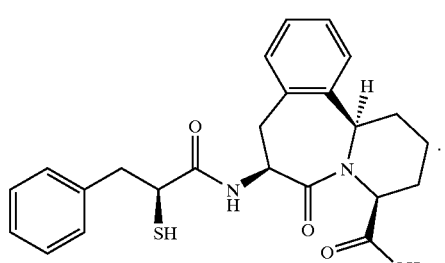
(Ib)

13. The process as claimed in claim 11, further comprising isolating (2R)-2-bromo-3-phenylpropionic acid in step (a).

14. The process as claimed in claim 11 wherein the thio reactant is thioacetate.

15. The process as claimed in claim 11 wherein $R_3$ is acetyl.

16. A process for the preparation of the compound of the formula (III)

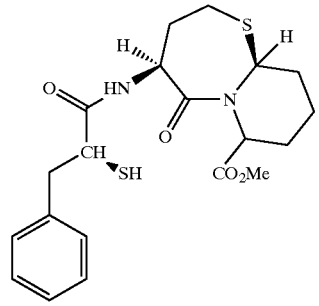
(III)

which comprises a) synthesizing (2R)-2-bromo-3-phenylpropionic acid from ethane-1,2-diaminium bis[(2R)-2-bromo-3-phenylpropanoate] by addition of an acid; then b) reacting (2R)-2-bromo-3-phenylpropionic acid with thioacetate to give (S)-2-(acetylthio)-3-phenylpropionic acid; and c) reacting (acetylthio)-3-phenylpropionic acid with a compound of the formula (IV)

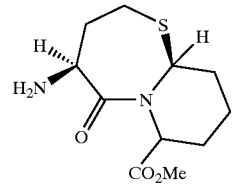
(IV)

to form a compound of formula (V)

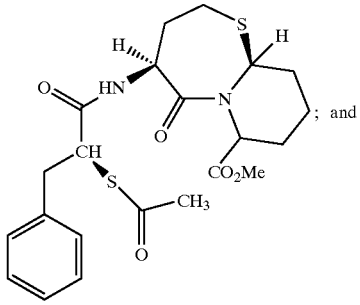
(V)
; and d) converting a compound of formula (V) to a compound of formula (Ill).

17. The process as claimed in claim 16, further comprising isolating (2R)-2-bromo-3-phenylpropionic acid in step (a).

* * * * *